(12) United States Patent
Yangdai et al.

(10) Patent No.: US 11,744,560 B2
(45) Date of Patent: Sep. 5, 2023

(54) SAMPLING CAPSULE

(71) Applicant: ANKON TECHNOLOGIES CO., LTD, Wuhan (CN)

(72) Inventors: Tianyi Yangdai, Wuhan (CN); Yuhui Bao, Wuhan (CN); Hangyu Peng, Wuhan (CN); Fanhua Ming, Wuhan (CN)

(73) Assignee: ANKON TECHNOLOGIES CO., LTD., Wuhan (CN)

( * ) Notice: Subject to any disclaimer, the term of this patent is extended or adjusted under 35 U.S.C. 154(b) by 561 days.

(21) Appl. No.: 16/929,119

(22) Filed: Jul. 15, 2020

(65) Prior Publication Data
US 2021/0015469 A1    Jan. 21, 2021

(30) Foreign Application Priority Data
Jul. 15, 2019   (CN) .......................... 201910636328.5

(51) Int. Cl.
*A61B 10/00*   (2006.01)
*A61B 1/273*   (2006.01)
*A61B 5/145*   (2006.01)

(52) U.S. Cl.
CPC .......... *A61B 10/0045* (2013.01); *A61B 1/273* (2013.01); *A61B 5/14539* (2013.01); *A61B 2010/0061* (2013.01)

(58) Field of Classification Search
CPC ..... A61B 10/0045; A61B 1/273; A61B 1/041; A61B 5/14539; A61B 5/073; A61B 2010/0061
See application file for complete search history.

(56) References Cited

U.S. PATENT DOCUMENTS

| | | | | |
|---|---|---|---|---|
| 3,057,344 | A | * | 10/1962 | Abella .................. A61B 10/02 604/93.01 |
| 2007/0161928 | A1 | * | 7/2007 | Sprenkels ......... B01L 3/502707 600/573 |
| 2009/0012503 | A1 | * | 1/2009 | Kawano ............. A61B 10/0045 604/891.1 |
| 2018/0164221 | A1 | * | 6/2018 | Singh .................... C12M 29/26 |

* cited by examiner

*Primary Examiner* — David J. McCrosky
*Assistant Examiner* — Nidhi N Patel
(74) *Attorney, Agent, or Firm* — Treasure IP Group, LLC

(57) ABSTRACT

A sampling capsule is provided. The sampling capsule includes an enclosure, a sampling assembly, a sample drawing assembly and a control module. The sampling assembly includes a sample chamber arranged in the enclosure, an outer sampling port on the enclosure, a sampling tube connecting the outer sampling port and the sample chamber, and a sampling switch for opening or closing the connecting tube. The sample drawing assembly includes a sample drawing port on the enclosure and connected to the sample chamber, and a silicone plug fitted in the sample discharging port. The control module includes a microprocessor communicating with the sampling switch.

9 Claims, 5 Drawing Sheets

SAMPLING CAPSULE

CROSS-REFERENCE OF RELATED APPLICATIONS

The application claims priority to Chinese Patent Application No. 201910636328.5 filed on Jul. 15, 2019, the contents of which are incorporated by reference herein.

FIELD OF INVENTION

The present invention relates to a medical device, and more particularly to a sampling capsule.

BACKGROUND

Due to high reliability and high safety, sampling capsule has become an effective device for the diagnosis of gastrointestinal diseases and has obtained high recognition in international medical device field. Generally, a sampling capsule comprises an enclosure, a sample chamber in the enclosure, and a sampling tube connected to the sample chamber. When the sampling capsule reaches a predetermined position in the gastrointestinal tract, the sampling tube is opened, and digestive fluids flow into the sample chamber. And after the sampling capsule is discharged, medical staff can take the digestive fluids out of the sample chamber for pathological analysis.

Before use of the existing sampling capsule, the sample chamber is under vacuum condition, and after the sampling tube is open, the digestive fluids enter the sample chamber under the pressure difference between inside and outside. However, if air leak occurs during transportation and storage, the sampling capsule can be scrapped, and sample drawing is cumbersome after completion of sampling.

In consideration of this, it is necessary to provide an improved sampling capsule to solve the problem.

SUMMARY OF THE INVENTION

The present invention provides a sampling capsule which can improve sampling effectiveness.

In order to achieve the object, the following technical solutions are employed.

A sampling capsule, comprising:

an enclosure; a sampling assembly comprising a sample chamber disposed in the enclosure, an outer sampling port on the enclosure, a sampling tube connecting the outer sampling port and the sample chamber, and a sampling switch for opening or closing the sampling tube;

a sample drawing assembly comprising a sample drawing port on the enclosure and connected to the sample chamber, and a silicone plug fitted in the sample drawing port; and a control module comprising a microprocessor in communication with the sampling switch.

In one embodiment, the sample drawing assembly further comprises a fixing member corresponding to the sample drawing port, and the silicone plug is fitted in the fixing member.

In one embodiment, the inner diameter of the fixing member gradually decreases from a first end to a second end, one end of the silicone plug protrudes from the second end of the fixing member, and the diameter of the protruding end of the silicone plug is greater than the diameter of the second end of the fixing member;

or both two ends of the silicone plug protrude from the fixing member, and both two ends of the silicone plug have a diameter greater than the inner diameter of the fixing member;

or the fixing member comprises a snap-on portion and a fixing portion adjacent to the snap-on portion, the inner diameter of the snap-on portion is smaller than the inner diameter of the fixing portion, and the inner diameter of the fixing portion gradually decreases from one end of the snap-on portion to the other end.

In one embodiment, when one end of the silicone plug protrudes from the fixing member, the end of the silicone plug near the sample chamber protrudes from the fixing member, and the diameter of the protruding end is greater than the inner diameter of the fixing member, and the inner diameter of the fixing member gradually decreases from outside to inside; or when the fixing member comprises the snap-on portion, the fixing member extends from the snap-on portion toward the sample chamber, the inner diameter of the snap-on portion is smaller than the inner diameter of the fixing portion, and the inner diameter of the fixing portion gradually decreases from outside to inside.

In one embodiment, the sample chamber is under vacuum condition with an absolute pressure between 0 hPa and 260 hPa.

In one embodiment, the control module further comprises a pressure sensor disposed in the sample chamber.

In one embodiment, the sampling tube comprises a flexible tube, and the sampling switch comprises a clamping ring for clamping at least part of the flexible tube and a heating element in communication with the microprocessor and capable of fusing the clamping ring.

In one embodiment, the sampling capsule further comprises a partition wall within the enclosure, and the partition wall together with the enclosure on a first side of the partition wall forms the sample chamber, and the outer sampling port is on a second side of the partition wall; and the sampling assembly further comprises an inner sampling port cut in the partition wall, one end of the flexible tube is connected to the inner sampling port and the flexible tube extends along the axis of the sampling capsule; and wherein the sampling tube further comprises a sample access tube connecting the flexible tube to the outer sampling port;

and the sampling capsule comprises a plurality of the outer sampling ports and the sample access tube comprises a multi-way tube connecting the plurality of outer sampling ports to the flexible tube.

In one embodiment, the plurality of the outer sampling ports are distributed along the circumference of the sampling capsule, and the sample access tube further comprises an annular tube connected to the plurality of the outer sampling ports, and the inlet of the multi-way tube is connected to the annular tube.

In one embodiment, the microprocessor and the flexible tube are disposed on opposite sides of the sample access tube, and the sample access tube comprises a penetration portion through which a wire passes, and the wire is communicatively connected to the heating element and the microprocessor.

Compared with the prior art, the present invention has the following beneficial effects: by the silicone plug, for one thing, if the sampling capsule leaks during transportation and storage, a syringe can be used to pierce the silicone plug to pump air out of the sample chamber again to achieve the desired vacuum, so as not to cause product waste; in addition, according to the shrinkage of the silicone plug, the needle eye is sealed after the syringe is pulled out, so that subsequent use is not be affected. For another, the sampling capsule can be produced without evacuating the sample chamber, but a syringe or the like is used to produce a desired vacuum in the sample chamber through the silicone plug.

DETAILED DESCRIPTION

Figure 1:
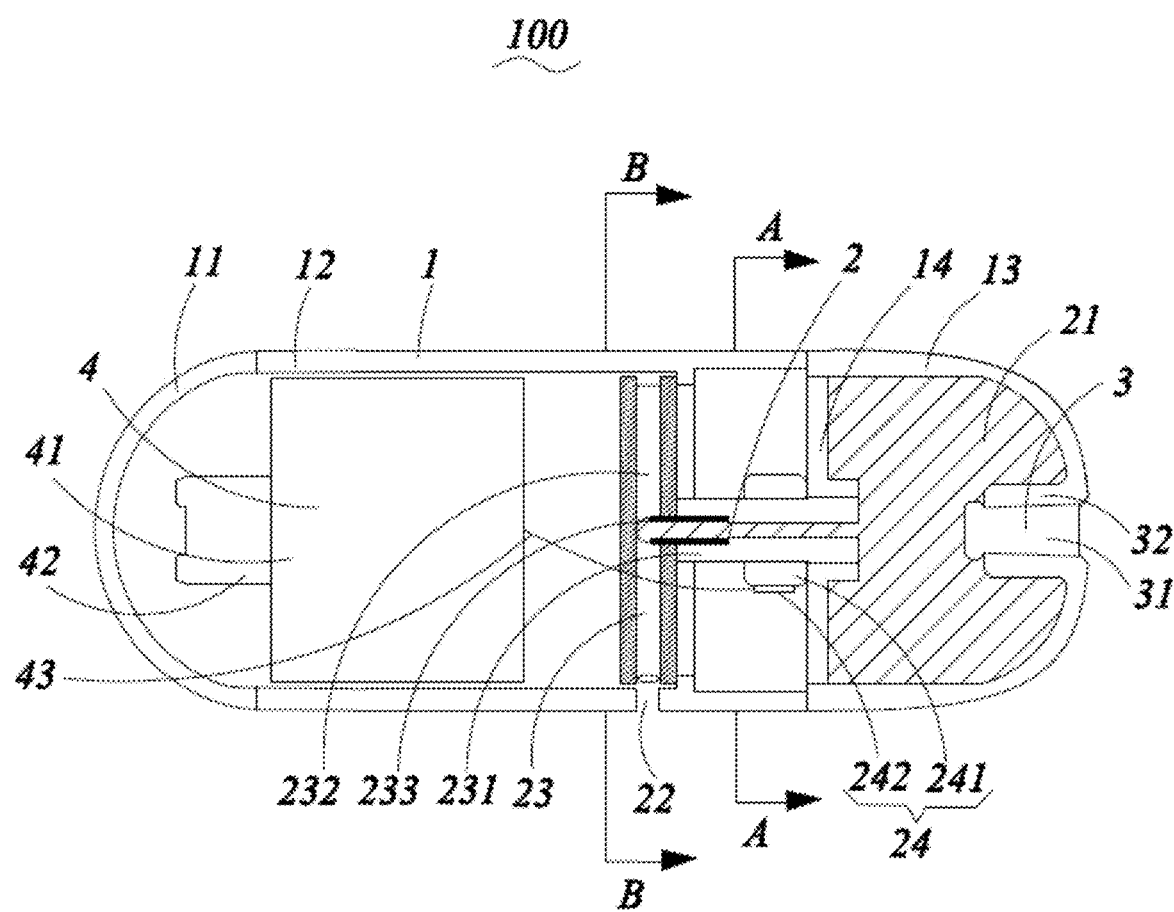
FIG. 1 shows an internal structural view of a sampling capsule according to a preferred embodiment of the present invention, where a sampling tube of the sampling capsule is in an open state.
Figure 2:
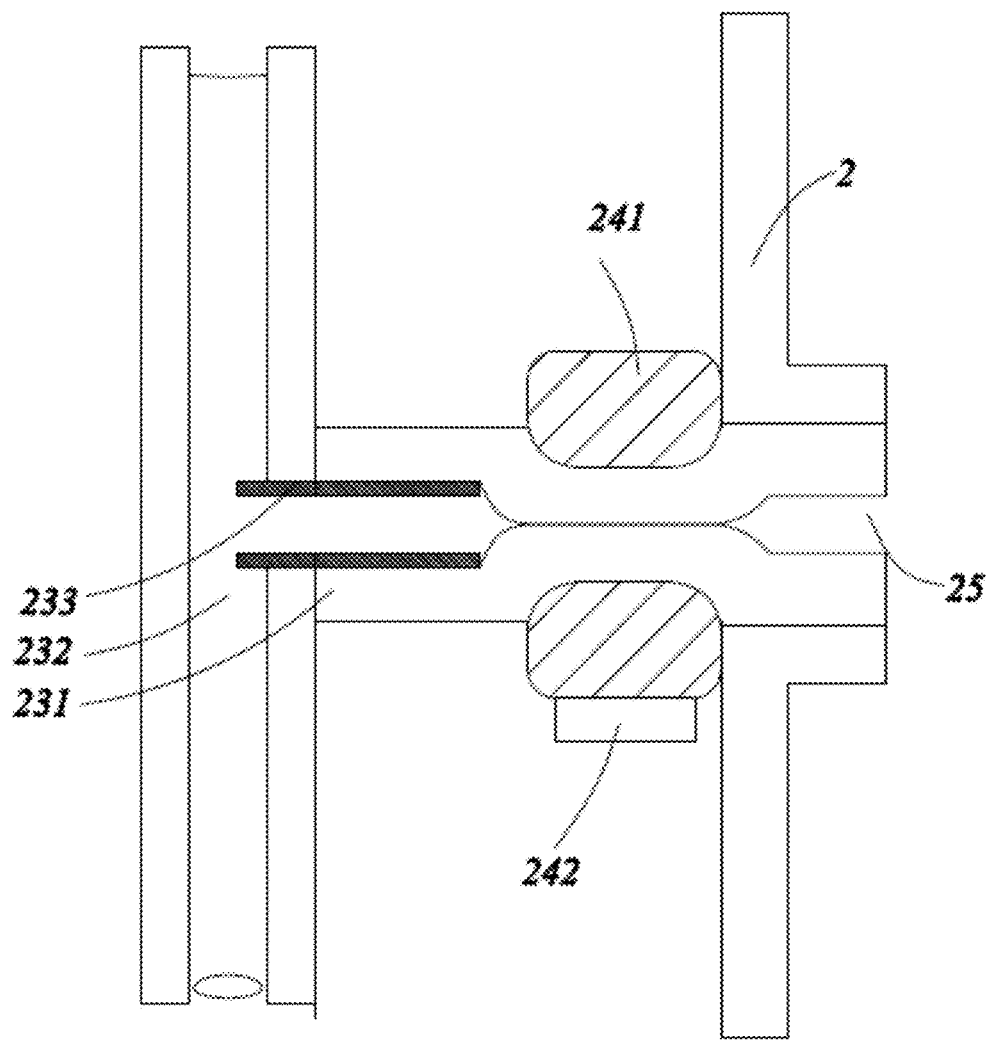
FIG. 2 is a structural view of the sampling tube in a closed state in the sampling capsule of FIG. 1.
Figure 3:
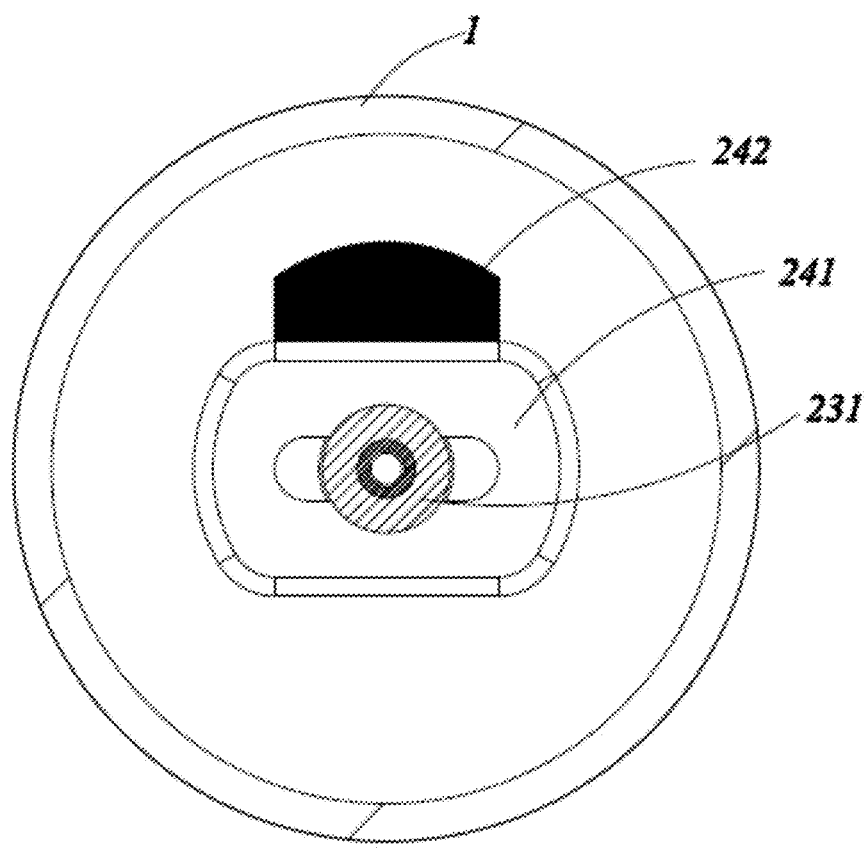
FIG. 3 is a cross sectional view of the sampling capsule of FIG. 1 in A-A direction, where the sampling tube is in a closed state.
Figure 4:
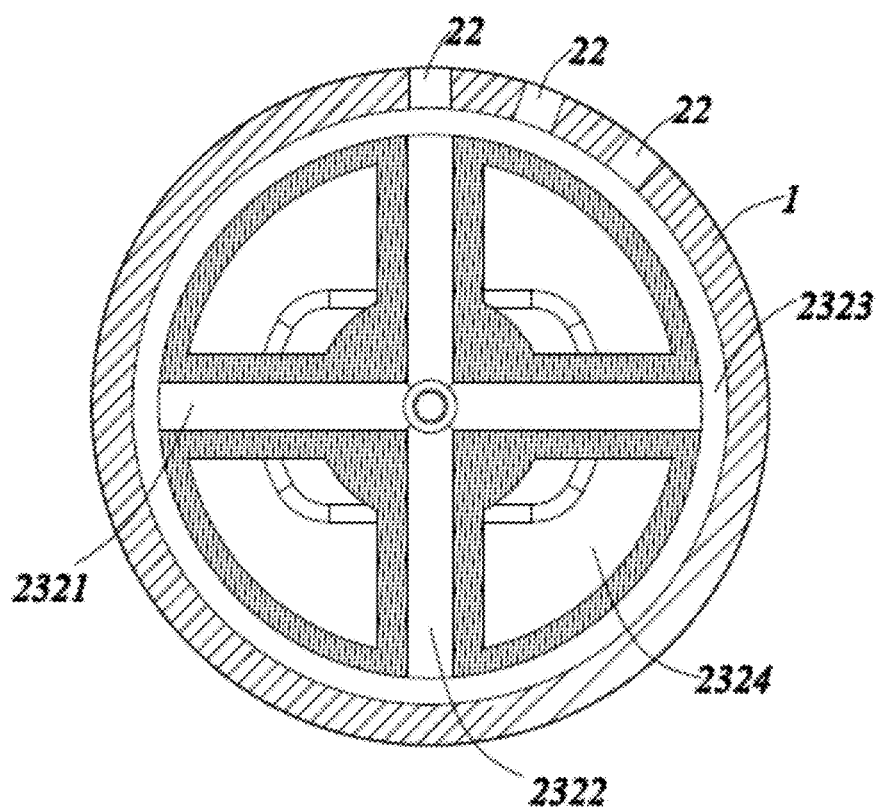
FIG. 4 is a cross sectional view of the sampling capsule of FIG. 1 in B-B direction, where the sampling tube is in a closed state.

The present invention can be described in detail below with reference to the accompanying drawings and preferred embodiments. Refer to FIGS. 1 to 5 for preferred embodiments of the present invention. However, it should be noted that these embodiments are not a limitation of the present invention, and that equivalent alterations or substitutions on function, method, or structure made by those of ordinary skill in the art according to these embodiments are all within the scope of protection of the present invention. In addition, "and/or" as used herein denotes "or" or "and", e.g., "M and/or N" comprises M, or N, or M and N.

Referring to FIGS. 1~5, showing a sampling capsule 100 and an internal structure thereof according to the preferred embodiments of the present invention.

The sampling capsule 100 comprises an enclosure 1, a sampling assembly 2, and a sample drawing assembly 3 and a control module 4. The control module 4 comprises a microprocessor in communication with one or more structures of the assemblies to control and/or coordinate the working state thereof.

The material of the enclosure 1 can be the material of the enclosure 1 of the existing sampling capsule 100, or can be additionally designed. It should be understood that the material of the enclosure 1 is acceptable as long as it is harmless to humans and cannot be corroded by digestive fluids.

Further, the enclosure 1 is constructed by at least two parts joined together to facilitate arrangement of internal components inside the enclosure 1. For example, as shown in FIG. 1, the enclosure 1 comprises a first enclosure 11, a second enclosure 12, and a third enclosure 13, and is formed by splicing the first enclosure 11, the second enclosure 12, and the third enclosure 13 together.

The sampling assembly 2 comprises a sample chamber 21 disposed in the enclosure 1, an outer sampling port 22 on the enclosure 1, a sampling tube 23 connecting the outer sampling port 22 and the sample chamber 21, and a sampling switch 24 for opening or closing the sampling tube 23.

Specifically, the sampling capsule 100 further comprises a partition wall 14 within the enclosure 1, and the partition wall 14 together with the enclosure 1 on a first side of the partition wall 14 forms the sample chamber 21. The outer sampling port 22, the sampling tube 23 and the sampling switch 24 are arranged on a second side of the partition wall 14.

Preferably, the enclosure 1 on the first side of the partition wall 14 is transparent to facilitate observation of sampling and sample drawing by a healthcare professional, and specifically observation of the amount of sampling and the remaining amount of sample after drawing.

The partition wall 14 is designed integrally with the enclosure 1 on the first side of the partition wall 14 to form the sample chamber 21 with a good leak tightness, or the partition wall 14 and the enclosure 1 on the first side of the partition wall 14 have a split-type design and the tightness at the junction of the two ensures that the sample chamber 21 can maintain its required vacuum degree.

Before use, the sample chamber 21 is sterilized, and the sample chamber 21 is under vacuum condition with an absolute pressure between 0 hPa and 260 hPa. When the sampling capsule 100 reaches a desired region in the gastrointestinal tract, the sampling tube 23 is opened, allowing the digestive fluid to enter the sample chamber 21 through the sampling tube 23 due to internal and external pressure difference.

Methods of evacuating the sample chamber 21 comprises, but are not limited to, opening the sampling tube 23 before completion of manufacturing, extracting air from the sample chamber 21 through the outer sampling port 22 by a pumping device, and after achieving a desired vacuum, closing the sampling tube 23 so that the sample chamber 21 maintains the desired vacuum; or, after completion of manufacturing, extracting air from the sample chamber 21 through the sample drawing assembly 3 by a pumping device to achieve a desired vacuum; or, before use, extracting air from the sample chamber 21 through the sample drawing assembly 3 by a pumping device to achieve a desired vacuum.

The sampling tube 23 comprises a flexible tube 231, and the sampling switch 24 comprises a clamping ring 241 for clamping at least part of the flexible tube 231, and a heating element 242 in communication with the microprocessor and capable of fusing the clamping ring 241. The sampling switch 24 opens or closes the flexible tube 231 to enable the opening or closing of the sampling tube 23.

Specifically, the sampling assembly 2 further comprises an inner sampling port 25 cut in the partition wall 14. One end of the flexible tube 231 is connected to the inner sampling port 25 and the flexible tube 231 extends along the axis of the sampling capsule 100. The sampling tube 23 further comprises a sample access tube 232 connecting the flexible tube 231 to the outer sampling port 22. The sampling capsule comprises a plurality of the outer sampling ports 22 and the sample access tube 232 comprises a multi-way tube 2321 connecting the plurality of outer sampling ports 22 to the flexible tube 231.

The end of the flexible tube 231 close to the inner sampling port 25 is inserted into the inner sampling port 25, and the other end of the flexible tube 231 away from the inner sampling port 25 is connected to the outlet of the sample access tube 232, so that after the heating element 242 fuses the clamping ring 241, the sample access tube 232, the flexible tube 231, and the sample chamber 21 are in an interconnected state, allowing the digestive fluids to enter the sample chamber 21 through the outer sampling port 22, the sample access tube 232, the flexible tube 231, and the inner sampling port 25.

In one embodiment, the sampling tube 23 further comprises a connecting tube 233 for connecting the outlet of the sample access tube 232 to the flexible tube 231 to facilitate the installation of the flexible tube 231 and to simplify the process of making the sampling tube 23. In addition, the flexible tube 231 can also be inserted directly into the outlet of the sample access tube 232 to provide connection and connectivity between the flexible tube 231 and the sample access tube 232.

Specifically, the connecting tube 233 is a rigid tube. One end of the connecting tube 233 is inserted into the outlet of the sample access tube 232 and has an interference fit to the outlet, and the other end of the connecting tube 233 is inserted into an end of the flexible tube 231 away from the inner sampling port 25 and has an interference fit to the flexible tube 231. The connecting tube 233 can connect the sample access tube 232 to the flexible tube 231, to facilitate the installation of the flexible tube 231, and to ensure the stability of the connection between the sample access tube 232 and the flexible tube 231 and the sealing of the connection between the two.

Further, the sampling capsule comprises a plurality of the outer sampling ports 22 and the sample access tube 232 comprises a multi-way tube 2321 connecting the plurality of outer sampling ports 22 and the flexible tube 231, to improve sampling efficiency and save time.

Specifically, the multi-way tube 2321 comprises a plurality of sub-tubes 2322, the plurality of sub-tubes 2322 being connected to the outlet of the sample access tube 232.

Further, the plurality of the outer sampling ports 22 are distributed along the circumference of the sampling capsule 100, the sample access tube 232 further comprises an annular tube 2323 connected to the plurality of the outer sampling ports 22, and the inlet of the multi-way tube 2321 is connected to the annular tube 2323. The digestive fluids entering from the outer sampling ports 22 flows first into the annular tube 2323 and then flows into the sample chamber 21 through the multi-way tube 2321, the flexible tube 231, and the inner sampling port 25.

It can be understood that, in the embodiment with the annular tube 2323, the number of the sub-tubes 2322 of the multi-way tube 2321 can be different from the number of the outer sampling ports 22. In the embodiment without the annular tube 2323, i.e., where the sub-tubes 2322 are directly connected to the corresponding outer sampling ports 22, the number of the sub-tubes 2322 of the multi-way tube 2321 is the same as the number of the outer sampling ports 22, that is, each sub-tube 2322 correspond to one outer sampling port 22.

Further, the microprocessor and the flexible 231 are disposed on opposite sides of the sample access tube 232 to rationalize the layout of the components within the sampling capsule 100.

In the embodiment where the microprocessor and the flexible tube 231 are disposed on opposite sides of the sample access tube 232, the sample access tube 232 comprises a penetration portion 2324 through which a wire 43 passes. The wire 43 can be communicatively connected to the heating element 242 and the microprocessor, so that the heating element 242 can communicate with the microprocessor through the wire 43.

It can be understood that in the embodiment where the sample access tube 232 comprises a multi-way tube 2321, the penetration portion 2324 is a gap between two adjacent sub-tubes 2322.

When the sampling capsule 100 is not in use or does not reach the desired region in the gastrointestinal tract, the clamping ring 241 clamps the corresponding flexible tube 231 to close the sampling tube 23 and maintain a vacuum in the sampling capsule 21. When the sampling capsule 100 reaches the desired region in the gastrointestinal tract, the clamping ring 241 is fused by the heating element 242, and the flexible tube 231 under the action of its own elastic recovery force recovers to tubular shape to open the sampling tube 23, so that the digestive fluids enter the sample chamber 21 through the outer sampling port 22, the sampling tube 23 and the inner sampling port 25 due to internal and external pressure difference. Actively controlled opening of the sampling tube 23 by the heating element 242 is independent of the particular environment in the gastrointestinal tract. Therefore, the invention has high versatility, and simplifies the internal structure of the sampling capsule 100 to reduce cost.

As sampling ends, the internal and external pressures of the sample chamber 21 are balanced. Also, the sampling tube 23 has a small diameter, such as 0.5 mm, so that, when the sampling tube 23 is in an open state, the digestive fluids in the sample chamber 21 has difficulty flowing out of the sampling capsule 100 through the sampling tube 23, ensuring that the collected digestive fluids can be maintained within the sample chamber 21.

In an embodiment, the clamping ring 241 is an alloy ring with a melting point between 42° C. and 55° C. In one aspect, the alloy ring has a hardness that allows it to be able to clamp the flexible tube 231 while bending, and the elastic recovery force of the flexible tube 231 is not sufficient to cause the alloy ring to deform, so that the alloy ring can remain tightly clamping the flexible tube 231 at all times to keep the sampling tube 23 closed and maintain a vacuum in the sample chamber 21. In other aspect, the alloy ring has a melting point between 42° C. and 55° C., which protects the alloy ring from being affected by the temperature in human body, and protects the human body from being harmed during fusing of the alloy ring by the heating element 242. But, it is not limited to this, provided that the clamping ring 241 can keep clamping the flexible tube 231 while bending and has a melting point between 42° C. and 55° C.

In the embodiment, the clamping ring 241 is in the shape of a closed ring, similar to a waist, and the clamping ring 241 has two opposite clamping portions to clamp the flexible tube 231. The heating element 242 is disposed on the outer periphery of the clamping portions to fuse the clamping portions, i.e. to fuse the clamping ring 241, so that the flexible tube 231 is able to recover to a tubular shape under the action of its own elastic recovery force and make the sampling tube 23 in an open state. Then, the digestive fluids enter the sample chamber 21 through the outer sampling port 22, the sampling tube 23 and the inner sampling port 25 under the pressure difference between inside and outside.

In other embodiments, the clamping ring 241 can also be non-closed. For example, the clamping ring 241 comprises two opposite clamping portions to clamp the flexible tube 231, and a connecting portion connecting the two clamping portions at an end of the same side. In this structure, the heating element 242 can be disposed on one of the clamping portions or on the connecting portion, provided that the flexible tube 231 can recover to a tubular shape under its own elastic recovery force after the heating element 242 fuses the clamping ring 241.

In an embodiment, the heating element 242 is a heating resistor, but is not limited thereto.

The sample drawing assembly 3 comprises a sample drawing port on the enclosure 1 and connected to the sample chamber 21, and a silicone plug 31 fitted in the sample drawing port. If the method of evacuating before the completion of manufacturing, when it is detected that the sampling capsule 100 leaks during transportation and storage, a syringe can be used to pierce the silicone plug 31 to pump air out of the sample chamber 21 again to achieve the desired vacuum, so as not to cause product waste. In addition, according to the shrinkage of the silicone plug, the needle eye is sealed after the syringe is pulled out, so that subsequent use cannot be affected. In one aspect, the sampling capsule 100 can be produced without evacuating the sample chamber 21, but before use, a syringe or the like is used to produce a desired vacuum in the sample chamber 21 through the silicone plug 31. All of the above methods ensure that the sample chamber 21 is used under the desired vacuum conditions to achieve optimum sampling of the sampling capsule 100.

Further, the sample drawing assembly 3 further comprises a fixing member 32 corresponding to the sample drawing port, and the silicone plug 31 is fitted in the fixing member 32. The fixing member 32 extends in the thickness direction of the enclosure 1, that is, the fixing member 32 extends into the sample chamber 21. The fixing member 32 fixes the silicone plug 31 to the sample drawing port, making up for the instability existing in the direct fixing of the thin enclosure 1 and the silicone plug 31, and maintaining a seal between the two when the silicone plug 31 is pierced by a syringe or the like.

Specifically, the fixing member 32 integrates with the enclosure 1, or the fixing member 32 is separate from the enclosure 1, and the two are sealed.

In addition, the silicone plug 31 has an interference fit to the fixture 32, easy for assembly.

The fixing member 32 comprises a first end and a second end. The inner diameter of the fixing member 32 gradually decreases from the first end to the second end, one end of the silicone plug 31 protrudes from the second end of the fixing member 32, and the diameter of the protruding end of the silicone plug 31 is greater than the diameter of the second end thereof. Specifically, in the embodiment shown in FIG. 1, the end of the silicone plug 32 close to the sample chamber 21 protrudes from the fixing member 32 and the diameter of the protruding end is greater than the inner diameter of the fixing member 32, and in the process of sampling, after the digestive fluids enter the sample chamber 21, the silicone plug 31 cannot be pushed out of the fixing member 32. In addition, the inner diameter of the fixing member 32 gradually decreases from outside to inside, which also prevents the silicone plug 31 from falling off during evacuating or sample drawing.

Or, both two ends of the silicone plug 31 protrude from the fixing member 32, and both two ends of the silicone plug 31 have a diameter greater than the inner diameter of the fixing member 32, which can prevent the silicone plug 31 from falling off during sampling, evacuating or sample drawing.

Figure 5:
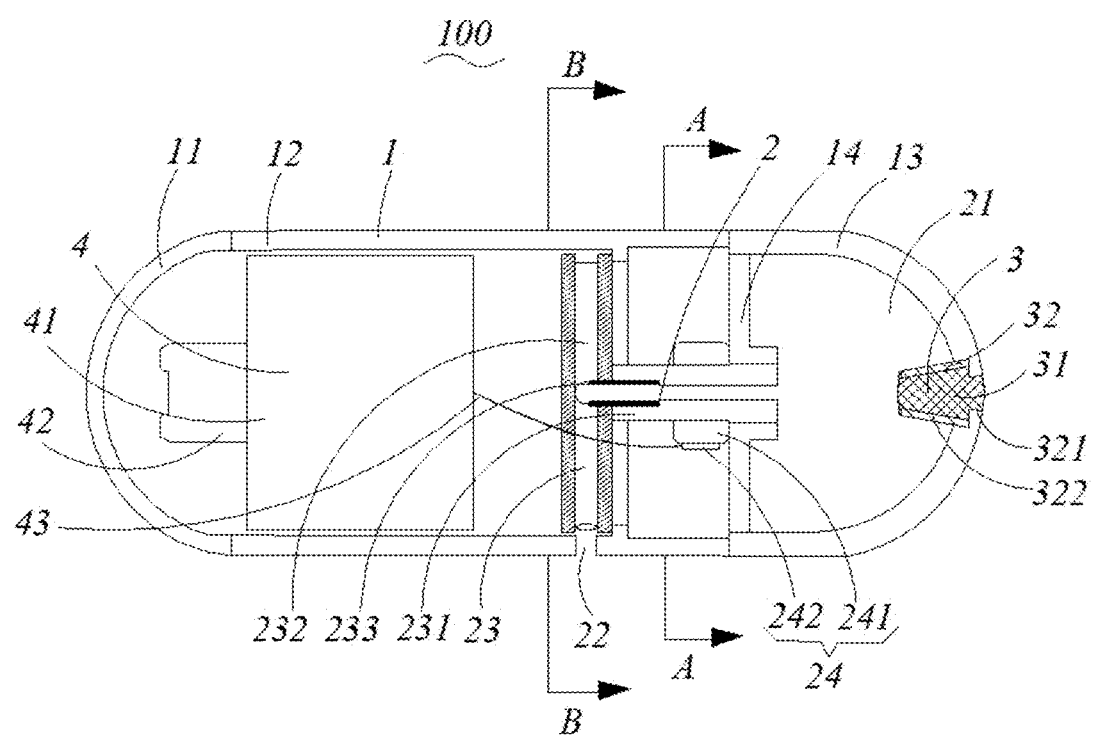
FIG. 5 shows the internal structural view of the sampling capsule according to another preferred embodiment of the present invention, where the sampling tube is in an open state.

Or, the fixing member 32 comprises a snap-on portion 321 and a fixing portion 322 adjacent to the snap-on portion 321, the inner diameter of the snap-on portion 321 is smaller than the inner diameter of the fixing portion 322, and the inner diameter of the fixing portion 322 gradually decreases from one end of the snap-on portion 321 to the other end. As shown in FIG. 5, the fixing member 32 has a snap-on portion 321 and a fixing portion 322 extending from the snap-on portion 321 toward the sample chamber 21, where the inner diameter of the snap-on portion 321 is smaller than the inner diameter of the fixing portion 322, and the inner diameter of the fixing portion 322 gradually decreases from outside to inside. Such structure can prevent the silicone plug 31 from falling off during sampling, evacuating or sample drawing.

In addition, the difference between the embodiment shown in FIG. 5 and the embodiment shown in FIG. 1 only lies in the sample drawing assembly 3, while the other structures are the same, and the sectional views along the A-A and B-B directions in FIG. 5 are also consistent with the sectional views along these two directions in FIG. 1, and is not repeated herein.

The control module 4 further comprises a pressure sensor 42 disposed within the sample chamber 21, and the pressure sensor 42 detects pressure within the sample chamber 21. The control module 4 determines whether the sampling capsule 100 is valid based on the pressure before taking the sampling capsule 100. The control module 4 can also determine whether the sampling capsule 100 is valid based on the pressure before sending sampling commands. The control module 4 can also determine whether the sampling is proceeding properly, and determine whether the sampling ends.

Further, the control module 4 further comprises a sensor 42 for collecting physiological parameters and/or image information in the gastrointestinal tract, and the sensor 42 communicates with the microprocessor. The sensor 42 can be one or more sensors selected from an image sensor, a pH sensor, or an ultrasonic sensor. When the sensor 42 comprises an image sensor, part of the enclosure 1 is transparent, and when the sensor 42 comprises a pH sensor, the enclosure 1 comprises a window. The specific method of determining which region of the gastrointestinal tract the sampling capsule 100 is in, based on the picture and pH value obtained by the sensor 42, can be any method in the prior art, and is not be repeated herein.

While the control module 4 comprises the sensor 42, the control module 4 can further comprise a storage module for storing normal physiological parameters or image information and physiological parameters or image information in case of possible lesions in different regions of the gastrointestinal tract, where the storage module communicates with the microprocessor. After the sensor 42 collects physiological parameters and/or image information in the gastrointestinal tract, the microprocessor compares the collected information with the stored information in the storage module to determine whether the sampling capsule 100 reaches the position at which the sample is to be taken.

Or, while the control module 4 comprises the sensor 42, the control module 4 further comprises a wireless transmission module for communicating with an external processing terminal. When the sensor 42 collects physiological parameters and/or image information in the gastrointestinal tract, it transmits the collected information to an external processing terminal, and the external processing terminal analyzes the collected information and determines whether the sampling capsule 100 reaches the position at which the sample is to be taken.

In addition, the control module 4 further comprises a battery that provides power to other components of the sampling capsule 100. The sampling capsule 100 further comprises a circuit board 41, and the microprocessor and the wireless transmission module are all integrated on the same circuit board 41.

The following can describe the operating process of the sampling capsule 100 of the present invention with an image sensor as an example.

The image sensor transmits the acquired images of the gastrointestinal tract to the external processing terminal, and the external processing terminal analyzes the acquired images of the gastrointestinal tract and identifies the position of the sampling capsule 100 in the gastrointestinal tract by means of visual check or a computer vision algorithm. In addition, a physician or the computer vision algorithm can identify the existence of some lesions by means of the images of the gastrointestinal tract, and thus determine whether sampling is required. If sampling is required, the external processing terminal sends a command to the microprocessor via the wireless transmission module, and when the microprocessor receives the command, the microprocessor controls the heating element 242 to heat and fuse the clamping ring 241 to open the sampling tube 23 for sampling.

Specifically, after determining that the sampling capsule 100 reaches a position where sampling is required, the external processing terminal can send an reminder message to the physician for confirmation, or can also directly send a need-to-sample command to the microprocessor via the wireless transmission module to start sampling.

Once the sampling is complete, the healthcare professional draws the sample fluids from the sample chamber 21 using a syringe or the like that is pierced into the sample chamber 21 through the silicone plug 31 for subsequent analysis and testing.

In summary, the sampling capsule 100 of the present invention comprises a silicone plug 31 connected to the sample chamber 21. Based on the silicone plug 31, for one thing, if the sampling capsule 100 leaks during transportation and storage, a syringe can be used to pierce the silicone plug 31 to pump air out of the sample chamber 21 again to achieve the desired vacuum, so as not to cause product waste. In addition, according to the shrinkage of the silicone plug 31, the needle eye is sealed after the syringe is pulled out, so that subsequent use is not be affected. For another, the sampling capsule 100 can be produced without evacuating the sample chamber, but a syringe or the like is used to produce the desired vacuum in the sample chamber 21 through the silicone plug 31.

It should be understood that, although the specification is described in terms of embodiments, not every embodiment merely includes an independent technical solution. Those skilled in the art should have the specification as a whole, and the technical solutions in each embodiment may also be combined as appropriate to form other embodiments that can be understood by those skilled in the art.

The present invention by no means is limited to the preferred embodiments described above. On the contrary, many modifications and variations are possible within the scope of the appended claims.

What is claimed is:

1. A sampling capsule, comprising:
an enclosure;
a sampling assembly comprising a sample chamber disposed in the enclosure, an outer sampling port on the enclosure, a sampling tube connecting the outer sampling port and the sample chamber, and a sampling switch for opening or closing the sampling tube;
a sample drawing assembly comprising a sample drawing port on the enclosure and connected to the sample chamber, and a silicone plug fitted in the sample drawing port; and
a control module comprising a microprocessor in communication with the sampling switch,
wherein the sampling tube comprises wherein the sampling tube comprises a flexible tube, and the sampling switch comprises a clamping ring for clamping at least part of the flexible tube and a heating element in communication with the microprocessor and capable of fusing the clamping ring.

2. The sampling capsule of claim 1, wherein the sample drawing assembly further comprises a fixing member corresponding to the sample drawing port, and the silicone plug is fitted in the fixing member.

3. The sampling capsule of claim 2, wherein the inner diameter of the fixing member gradually decreases from a first end to a second end, one end of the silicone plug protrudes from the second end of the fixing member, and the diameter of the protruding end of the silicone plug is greater than the diameter of the second end of the fixing member; or
wherein both two ends of the silicone plug protrude from the fixing member, and both two ends of the silicone plug have a diameter greater than the inner diameter of the fixing member; or
wherein the fixing member comprises a snap-on portion and a fixing portion adjacent to the snap-on portion, the inner diameter of the snap-on portion is smaller than the inner diameter of the fixing portion, and the inner diameter of the fixing portion gradually decreases from one end of the snap-on portion to the other end.

4. The sampling capsule of claim 3, wherein when one end of the silicone plug protrudes from the fixing member, the end of the silicone plug near the sample chamber protrudes from the fixing member, and the diameter of the protruding end is greater than the inner diameter of the fixing member, and the inner diameter of the fixing member gradually decreases from outside to inside; or
wherein when the fixing member comprises the snap-on portion, the fixing member extends from the snap-on portion toward the sample chamber, the inner diameter of the snap-on portion is smaller than the inner diameter of the fixing portion, and the inner diameter of the fixing portion gradually decreases from outside to inside.

5. The sampling capsule of claim 1, wherein the sample chamber is vacuum with an absolute pressure between 0 hPa and 260 hPa.

6. The sampling capsule of claim 1, wherein the control module further comprises a pressure sensor disposed in the sample chamber.

7. The sampling capsule of claim 1, wherein the sampling capsule further comprises a partition wall within the enclosure, and the partition wall together with the enclosure on a first side of the partition wall forms the sample chamber, and the outer sampling port is on a second side of the partition wall; and
wherein the sampling assembly further comprises an inner sampling port cut in the partition wall, one end of the flexible tube is connected to the inner sampling port and the flexible tube extends along the axis of the sampling capsule; and wherein the sampling tube further comprises a sample access tube connecting the flexible tube to the outer sampling port; and
wherein the sampling capsule comprises a plurality of the outer sampling ports and the sample access tube comprises a multi-way tube connecting the plurality of outer sampling ports to the flexible tube.

8. The sampling capsule of claim 7, wherein the plurality of the outer sampling ports are distributed along the circumference of the sampling capsule, and the sample access tube further comprises an annular tube connected to the plurality of the outer sampling ports, and the inlet of the multi-way tube is connected to the annular tube.

9. The sampling capsule of claim 7, wherein the microprocessor and the flexible tube are disposed on opposite sides of the sample access tube, and the sample access tube comprises a penetration portion through which a wire passes, and the wire is communicatively connected to the heating element and the microprocessor.

\* \* \* \* \*